United States Patent [19]

Andrean et al.

[11] Patent Number: 5,645,609
[45] Date of Patent: Jul. 8, 1997

[54] COMPOSITIONS WHICH CONTAIN AND PROCESSES WHICH USE AN INSOLUBLE PIGMENT OBTAINED BY THE OXIDATIVE POLYMERIZATION OF INDOLE DERIVATIVES FOR THE TEMPORARY DYEING OF KERATINOUS FIBERS

[75] Inventors: Hervé Andrean, Paris; Alex Junino; Louis Lezoray, both of Livry-Gargan; Jean Cotteret, Verneuil-sur-Seine; Marie Pascale Audousset, Levallois-Perret; Mireille Maubru, Chatou, all of France

[73] Assignee: L'Oreal, Paris, France

[21] Appl. No.: 616,935

[22] Filed: Mar. 18, 1996

Related U.S. Application Data

[63] Continuation of Ser. No. 190,094, May 13, 1994, abandoned.

[30] Foreign Application Priority Data

Aug. 1, 1991 [FR] France ................... 91 09823

[51] Int. Cl.$^6$ .................... A61K 7/13
[52] U.S. Cl. .......... 8/405; 8/406; 8/423; 8/435; 8/552; 8/553; 8/555; 8/557; 8/558; 8/559; 8/561; 8/637.1; 106/493; 106/498
[58] Field of Search .................. 8/405, 406, 423, 8/435, 552, 553, 554, 558, 559, 561, 619, 637.1, 647, 555, 557; 106/493, 498

[56] References Cited

U.S. PATENT DOCUMENTS

| | | | |
|---|---|---|---|
| 4,806,360 | 2/1989 | Leony et al. | 424/59 |
| 4,888,027 | 12/1989 | Grollier et al. | 8/423 |
| 4,900,326 | 2/1990 | Grollier | 8/423 |
| 4,961,754 | 10/1990 | Grollier | 8/423 |
| 5,053,053 | 10/1991 | DeLabbey et al. | 8/423 |
| 5,064,442 | 11/1991 | Grollier | 8/423 |
| 5,120,325 | 6/1992 | Dow, Jr. | 604/304 |
| 5,180,400 | 1/1993 | Baudry et al. | 8/423 |
| 5,205,837 | 4/1993 | Andrean et al. | 8/423 |
| 5,207,798 | 5/1993 | Cotteret et al. | 8/423 |
| 5,227,459 | 7/1993 | Pawelek et al. | 424/59 |
| 5,244,497 | 9/1993 | Junino et al. | 8/423 |
| 5,279,620 | 1/1994 | Junino et al. | 8/423 |

FOREIGN PATENT DOCUMENTS

| | | |
|---|---|---|
| 0313380 | 4/1989 | European Pat. Off. . |
| 0376776 | 7/1990 | European Pat. Off. . |
| 0379409 | 7/1990 | European Pat. Off. . |
| 0467767 | 1/1992 | European Pat. Off. . |
| 2207153 | 1/1989 | United Kingdom . |
| 9001919 | 3/1990 | WIPO . |

OTHER PUBLICATIONS

English language translation of EP 379,409, L'Oreal, Jul. 1990, pp. 1–36.

*Primary Examiner*—Paul Lieberman
*Assistant Examiner*—Caroline L. Dusheck
*Attorney, Agent, or Firm*—Jacobson, Price, Holman & Stern, PLLC

[57] ABSTRACT

Process for the temporary dyeing of keratinous fibers with a composition containing an insoluble pigment obtained by the oxidative polymerization of an indole compound of formula (I)

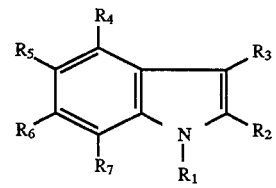

in which $R^1$ and $R^3$ are hydrogen or alkyl; $R^2$ is hydrogen, alkyl carboxyl or alkoxy carbonyl; $R^4$ and $R^7$ are hydrogen, hydroxy, alkyl, amino, alkoxy, acyloxy or acylamino; $R^5$ is hydrogen, hydroxy, alkoxy, alkyl, halogen, amino, acyloxy, acylamino or trimethylsilyloxy; $R^6$ is hydrogen, hydroxy, alkoxy, amino, acyloxy, acylamino, trimethylsilyloxy or hydroxyalkylamino; $R^5$ and $R^6$ can also form, together with the carbon atoms to which they are attached, a carbonyldioxy ring; at least one of the radicals $R^4$ to $R^7$ is an OZ or $NHR^8$ grouping, the $R^8$ radical of the $NHR^8$ grouping being hydrogen, acyl or hydroxyalkyl and the Z radical of the OZ grouping being hydrogen, acyl, alkyl or a trimethylsilyl group.

22 Claims, No Drawings

COMPOSITIONS WHICH CONTAIN AND PROCESSES WHICH USE AN INSOLUBLE PIGMENT OBTAINED BY THE OXIDATIVE POLYMERIZATION OF INDOLE DERIVATIVES FOR THE TEMPORARY DYEING OF KERATINOUS FIBERS

This application is a continuation of application Ser. No. 08/190,094, filed May 13, 1994, now abandoned.

The present invention relates to a process for the temporary dyeing of keratinous fibers, employing a composition containing at least one insoluble pigment obtained by the oxidative polymerization of indole derivatives.

Essentially three types of process are known for dyeing keratinous fibers such as hair, which consist of:

a) so-called permanent dyeing, the function of which is to bring about a substantial modification of the natural color, and which employs oxidation dyes which penetrate the keratinous fiber and form the dye by a process of oxidative condensation;

b) semi-permanent or direct dyeing; this dyeing does not employ the process of oxidative condensation, and withstands 4 to 5 shampooings.

c) temporary or fugitive dyeing gives rise to a slight modification of the natural color of the hair, which holds from one shampooing to the next and which serves to make more attractive or to correct a hue already obtained.

The invention relates to a dyeing process of the last type, resulting in a coloration which can be removed at the first shampooing. It may also be likened to a process "for making up keratinous fibers".

To modify hair and make it more attractive on a temporary basis, dyeing with direct dyes has already been proposed, but this dyeing can be heterogeneous on the parts of the hair which have been damaged by various degradations due to treatments such as, for example, permanent-waving, heat or environmental agents (sun, inclement weather). Moreover, these dyes do not generally make it possible to obtain a natural and attractive gray hue, except by using a mixture with other dyes which possess, however, the drawback that they often have different resistances to light or to shampooing, thereby giving rise to unsatisfactory final colorations. Lastly, this type of dye is not sufficiently good at making white hairs less noticeable; thereby constituting a further drawback.

It has also been proposed to use colored polymers formed by grafting one or more azo, triphenylmethane, azine, indamine or anthraquinone type dyes onto a polymer chain. These colored polymers are not completely satisfactory, in particular in respect of the homogeneity of the coloration obtained and its resistance, not to mention the problems linked to the manufacture of this type of colored polymer, in particular as regards their reproducibility.

The Applicant's objective was to find a means of temporarily dyeing keratinous fibers, especially hair. He looked, in particular, for compositions enabling the yellowness to be cleared from white hairs so that they could be given a natural and attractive gray hue. The coloration should, in particular, make white hairs less noticeable; the colorant should hence be sufficiently substantive to mask white hairs without being excessively so, especially on sensitized fibers, so that it can be readily removed at the first shampooing while withstanding brushing a large number of times and friction and does not stain clothing and pillows.

Indole dyes, and in particular 5,6-dihydroxyindole, which have already been recommended for dyeing keratinous fibers, in particular hair, employing a process of oxidative development, either in the presence of aerial oxygen or in the presence of various oxidizing agents or oxidation catalysts, are, moreover, known. The dyeing in this case is one which may be likened to so-called permanent dyeing, inasmuch as the dye develops inside the fiber following the action of the oxidizing agents or oxidation catalysts.

The subject of the present invention is the application to keratinous fibers of an insoluble pigment resulting from the oxidative polymerization of an indole derivative.

Insoluble pigment denotes a pigment which is insoluble in the cosmetically acceptable media used for temporary dyeing. The Applicant discovered that compositions containing such pigments enabled a temporary coloration to be imparted to keratinous fibers, and especially to hair, which could be removed at the first shampooing but nevertheless withstood brushing, styling a large number of times and friction and did not stain clothing. The compositions according to the invention containing the pigments defined below, and which take the form, in particular, of gels, enable a coloration to be obtained which does not powder on brushing.

The pigment used according to the invention displays with respect to keratinous fibers a sufficiently high substantivity to mask white hairs and make them less noticeable.

The subject of the invention is the use of an insoluble pigment originating from the oxidative polymerization of an indole compound, for the temporary dyeing of keratinous fibers.

The subject of the invention is also compositions intended for use in a process for the temporary dyeing of keratinous fibers.

Other subjects of the invention will become apparent on reading the description and the examples which follow.

The pigment used according to the invention, for the temporary dyeing of keratinous fibers, is characterized in that it is an insoluble pigment resulting from the oxidative polymerization of an indole compound corresponding to the formula (I):

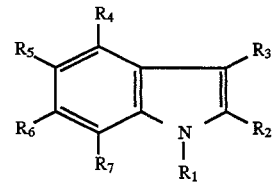

in which:

$R^1$ and $R^3$ represent, independently of one another, a hydrogen atom or a $C_1$–$C_4$ alkyl group;

$R^2$ represents a hydrogen atom, a $C_1$–$C_4$ alkyl group, a carboxyl group or a ($C_1$–$C_4$ alkoxy)carbonyl group;

$R^4$ and $R^7$ represent, independently of one another, a hydrogen atom, a hydroxyl group, a $C_1$–$C_4$ alkyl group, an amino group, a $C_1$–$C_4$ alkoxy group, a ($C_2$–$C_4$ acyl)oxy group or a ($C_2$–$C_4$ acyl) amino group;

$R^5$ represents a hydrogen atom, a hydroxyl group, a $C_1$–$C_4$ alkoxy group, a $C_1$–$C_4$ alkyl group, a halogen atom, an amino group, a ($C_2$–$C_4$ acyl)oxy group, a ($C_2$–$C_4$ acyl)amino group or a trimethylsilyloxy group;

$R^6$ represents a hydrogen atom, a hydroxyl group, a $C_1$–$C_4$ alkoxy group, an amino group, a ($C_2$–$C_4$ acyl)oxy group, a ($C_2$–$C_4$ acyl)amino group, a trimethylsilyloxy group or a hydroxy($C_2$–$C_4$ alkyl)amino group;

it not being possible for $R^5$ and $R^6$ simultaneously to designate a $C_1$–$C_4$ alkoxy radical;

it also being possible for $R^5$ and $R^6$, together with the carbon atoms to which they are attached, to form a carbonyldioxy ring;

at least one of the radicals $R^4$ to $R^7$ represents a group OZ or $NHR^8$, at most one of the radicals $R^4$ to $R^7$ representing $NHR^8$ and at most two of the radicals $R^4$ to $R^7$ representing OZ, and, in the case where Z represents a hydrogen atom, the two OH groups are in positions 5 and 6; and at least one of the radicals $R^4$ to $R^7$ represents a hydrogen atom and, in the case where only one of these radicals $R^4$ to $R^7$ represents a hydrogen atom, then only one radical from among $R^4$ to $R^7$ then represents $NHR^8$ or OZ, the other radicals representing a $C_1$–$C_4$ alkyl group;

the radical $R^8$ of the group $NHR^8$ denoting a hydrogen atom or a $C_2$–$C_4$ acyl or $C_2$–$C_4$ hydroxyalkyl group, and the radical Z of the group OZ denoting a hydrogen atom, a $C_2$–$C_{14}$ acyl group, a $C_1$–$C_4$ alkyl group or a trimethylsilyl group, and their alkali metal, alkaline earth metal, ammonium or amine salts.

The indole compounds of formula (I) above are chosen from 4-hydroxyindole, 5-hydroxyindole, 6-hydroxyindole, 7-hydroxyindole, 4-hydroxy- 5-methoxyindole, 4-hydroxy-5-ethoxyindole, 2-carboxy-5-hydroxyindole, 5-hydroxy-6-methoxyindole, 6-hydroxy-7-methoxyindole, 5-methoxy-6-hydroxyindole, 5,6-dihydroxyindole, N-methyl-5,6-dihydroxyindole, 2-methyl-5,6-dihydroxyindole, 3-methyl-5,6-dihydroxyindole, 2,3-dimethyl-5,6-dihydroxyindole, 2-carboxy-5,6-dihydroxyindole, 4-hydroxy-5-methylindole, 2-carboxy-6-hydroxy [sic], 6-hydroxyindole [sic], N-methylindole [sic], 2-ethoxycarbonyl-5,6-dihydroxyindole, 4-hydroxy-7-methoxy-2,3-dimethylindole, 4-hydroxy-5-ethoxy-N-methylindole, 6-hydroxy-5-methoxy-2-methylindole, 6-hydroxy-5-methoxy-2,3-dimethylindole, 6-hydroxy-2-ethoxycarbonylindole, 7-hydroxy-3-methylindole, 5-hydroxy-6-methoxy-2,3-dimethylindole, 5-hydroxy-3-methylindole, 5-acetoxy-6-hydroxyindole, 5-hydroxy-2-ethoxycarbonylindole, 6-hydroxy-2-carboxy-5-methylindole, 6-hydroxy-2-ethoxycarbonyl-5-methoxyindole, 6-[N-(β-hydroxyethyl)amino]-indole, 4-aminoindole, 5-aminoindole, 6-aminoindole, 7-aminoindole, N-methyl-6-(β-hydroxyethylomino)indole [sic], 6-amino-2,3-dimethylindole, 6-amino-2,3,4,5-tetramethylindole, 6-amino-2,3,4-trimethylindole, 6-amino-2,3,5-trimethylindole, 6-amino-2,3,6-trimethyl indole, 5,6-diacetoxyindole, 5-methoxy-6-acetoxyindole, 5,6-trimethylsilyloxyindole, 5,6-dihydroxyindole phosphoric ester, 5,6-dibenzyloxyindole and the addition salts of these compounds.

Especially preferred indole compounds are: 5,6-dihydroxyindole, 6-hydroxyindole, 7-hydroxyindole, 2-methyl -5,6-dihydroxyindolehydrobromide, 7-aminoindole, 3-methyl-5,6-dihydroxyindole, 4-hydroxy-5-methoxyindole and 2,3-dimethyl-5-methoxy-6-hydroxyindole.

The oxidative polymerization of the compounds of the formula (I) may be performed in an aqueous, water/solvent (s) or solvent(s) medium in the air, in the presence or absence of an alkaline agent and/or of an oxidizing agent such as hydrogen peroxide, preferably in the presence of an alkaline agent such as aqueous ammonia or in the presence of an iodide ion, the iodide preferably being an alkali metal, alkaline earth metal or ammonium iodide.

The oxidation of the compound of formula (I) may also be performed using periodic acid, its water-soluble salts and its derivatives, permanganates and dichromates such as those of sodium or potassium, sodium hypochlorite, ammonium persulfate, sodiumnitrite and organic oxidizing agents chosen from ortho- and para-benzoquinones, ortho- and para-benzoquinone mono- or diimines, 1,2-and 1,4-naphthoquinones and 1,2- and 1,4-naphthoquinone mono- or diimines as are described in Application EP-A-0,376,776. The preferred periodic acid salt is sodium periodate.

It is possible to activate the oxidizing agents with a pH modifier.

According to the invention, the preferred oxidative polymerization process employs hydrogen peroxide in the presence of aqueous ammonia. This oxidation reaction is generally performed at an ambient temperature of the order of 20° C. to 100° C., and preferably 60° C. to 90° C.

The implementation of the oxidative polymerization preferably takes place by introducing the indole compound of formula (I) into an aqueous medium, or into a mixture of water and one or more solvents which can contain up to 95% of solvent, or alternatively into one or more anhydrous solvent(s), that is to say which contain less than 1% of water.

Among solvents which can be used, there may be mentioned $C_1$–$C_4$ lower alcohols such as ethyl alcohol, propyl alcohol or isopropyl alcohol, tert-butyl alcohol, alkylene glycols such as ethylene glycol, propylene glycol, alkylene glycol alkyl ethers such as ethylene glycol monomethyl, monoethyl or monobutyl ethers, propylens glycol and dipropylene glycol monomethyl ethers, and esters such as methyl lactate. The preferred solvent medium is an aqueous-alcoholic medium containing from 1 to 10% of ethyl alcohol.

Depending on the process, the oxidizing agent and the indole compound of formula (I) are left in contact for a few minutes to a few days.

The alkalinizing agents are preferably chosen from sodium hydroxide, alkali metal carbonates and aqueous ammonia, in proportions of between $5 \times 10^{-4}\%$ and 10% by weight relative to the weight of the composition subjected to oxidation.

When an iodide is used in the presence of hydrogen peroxide, it is preferable to use a sodium or potassium iodide at a concentration of between 1 and 6%.

The colored pigment resulting from the oxidative polymerization is obtained in insoluble form. It is isolated by filtration or centrifugation. In order to remove the traces of unreacted compound of formula (I), the pigment may be rinsed with water before or after filtration or centrifugation.

In the case where an oxidative polymerization process is carried out in the air, it is also possible to isolate the pigment by lyophilization.

In order to obtain a homogeneous pigment of sufficiently fine particle size, it is possible to treat the product obtained following the oxidative polymerization by conventional grinding systems using the dry or wet method. It is also possible to use a micronization process.

The particle size of the final pigment is generally such that 90% of the particles have a diameter of less than 100 μm, and preferably less than 50 μm. The average particle diameter is preferably less than 50 μm, and especially less than 20 μm.

The insoluble pigments thereby obtained are used in compositions for dyeing keratinous fibers at weight concentrations generally of between 0.05 and 10%, and preferably between 0.2 and 2%, by weight relative to the total weight of the composition.

These temporary dyeing compositions are generally aqueous. They can, however, contain one or more solvents chosen from lower alcohols such as, for example, isopropanol or ethanol, polyols such as propylene glycol or glycerol, glycol ethers such as, for example, ethylene glycol monomethyl, monoethyl or monobutyl ethers, propylene glycol or dipropylene glycol or tripropylene glycol monomethyl ethers, or esters such as metyl [sic] lactate.

These solvents are generally present in weight proportions of between 1 and 75%, and preferably between 2 and 50%, relative to the total weight of the composition.

According to a preferred embodiment, the compositions according to the invention can contain a suspending agent for the pigments or a thickening agent in order to facilitate homogeneous distribution of the insoluble pigment in the composition and on the keratinous fibers.

These suspending or thickening agents may be chosen from cellulose derivatives such as, for example, carboxymethylcellulose or hydroxyethyl- or hydroxypropylcellulose, biopolysaccharides such as xanthan gums or scleroglucans, guar gum or inorganic thickeners such as clay derivatives or silicas.

It is also possible to use the products resulting from the ionic interaction of a cationic polymer, formed from a copolymer of cellulose or of a cellulose derivative grafted with a water-soluble quaternary ammonium monomer salt, and a carboxylic anionic polymer, as are described in French Patent FR 2,598,611. It is preferable to use the product of ionic interaction of a copolymer of hydroxyethylcellulose grafted by a free-radical method with diallyldimethylammonium chloride, such as the polymer marketed under the name CELQUAT L 200 by the company National Starch, either with copolymers of ethylene and maleic anhydride such as the products sold under the name EMA 31 by the company MONSANTO, or with 50/50 copolymers of methacrylic acid and methyl methacrylate.

Another product of this type which can be used is the product resulting from the ionic interaction of the copolymer of hydroxyethylcellulose grafted by a free-radical method with diallyldimethylammonium chloride with a crosslinked carboxylic anionic polymer such as the crosslinked copolymers of methacrylic acid and ethyl acrylate sold under the name VISCOATEX 538 or 46 by the company COATEX.

It is also possible to use for this purpose aqueous dispersions of ammonium acrylate/acrylamide copolymer crosslinked with a crosslinking agent containing olefinic polyunsaturation, dispersed in a water-in-oil emulsion comprising paraffin and a mixture of sorbitan stearate and hydrophilic ethoxylated derivative, and more especially the emulsion marketed under the name PAS 5161 by the company HOECHST, and comprising the ammonium acrylate/acrylamide copolymer (95:5 by weight). This commercially available composition contains 30% by weight of this copolymer, 25% by weight of paraffin, 4% of mixture of sorbitan and hydrophilic ethoxylated derivative and 41% of water.

Another thickening and/or suspending agent for the insoluble pigments used according to the invention consists of copolymers of methyl vinyl ether and maleic anhydride, crosslinked or otherwise, such as the neutralized product sold under the name GANTREZ ACV, or crosslinked polyacrylic acids such as the products sold under the name CARBOPOL by the company GOODRICH, or crosslinked copolymers of acrylic acid and long-chain (C10–C30) alkyl methacrylate or acrylate, sold, respectively, under the name CARBOPOL 1342 and PEMULEN TR-1 and TR-2 by the company GOODRICH. Crosslinked copolymers are preferably used.

These thickening agents are generally used in the temporary dyeing compositions according to the invention in proportions of between 0.05 and 10% by weight relative to the total weight of the compositions.

In a preferred embodiment of the invention, a film-forming latex, which enables temporary dyeing compositions displaying better resistance to brushing and imparting a superior sheen to the treated fibers, is used in the compositions containing the insoluble pigment originating from the oxidative polymerization of the compounds of formula (I). These latices may be present in proportions of between 0.1 and 5% by weight relative to the total weight of the composition.

A film-forming latex denotes a latex, 100 ml of a solution of which at a concentration of 8 g/100 ml, deposited in a strictly horizontal matrix of surface area 65 $cm^2$, discloses to the naked eye after 15 hours of drying at room temperature a fine homogeneous film which is uniform over the entire surface of the matrix. This latex is chosen, in particular, from;

homopolymers and copolymers of vinyl acetate, such as: poly(vinyl acetate), for instance the products sold under the names "Emulsion RHODOPAS AO12P" "Emulsion RHODOPAS AO13P" by the company RHONE POULENC; copolymers of vinyl acetate and ethylene, such as the products sold under the names "APPRETAN MB", "APPRETAN EM", "APPRETAN TV" by the company HOECHST.

homopolymers or copolymers derived from acrylic acid, such as the products sold under the names "PRIMAL AC-33, "PRIMAL K-3", "PRIMAL TR-93", "PRIMAL HA-8", "PRIMAL E-358", marketed by the company RHOM & HAAS;

polyurethanes, such as those sold under the name "WITCOBOND 160", "WITCOBOND 170" by the company WITCO.

butadiene/styrene copolymers, carboxylated or otherwise, such as the products sold under the names "Emulsion RHODOPAS SB02, "Emulsion RHODOPAS STY246", "Emulsion RHODOPAS SB153", "Emulsion RHODOPAS GB012" by the company RHONE POULENC;

butadiene/acrylonitrile copolymers, carboxylated or otherwise, such as the products sold under the names "HYCAR 1562" by the company GOODRICH and "CHEMIGUM L6271" by the company GOODYEAR;

stytens/acrylic esters copolymers, such as the product sold under the name "APPRETAN V3749" by the company HOECHST;

vinyl acetate/acrylic esters copolymers, such as the product sold under the name "Emulsion RHODOPAS AD 310";

styrene/butadiene/vinylpyridine terpolymers, such as the product sold under the name HYCAR 2508 by the company GOODRICH;

copolymers of vinyl chloride or of vinylidene chloride, such as the products sold under the names GEON 351 or 577 by the company GOODRICH.

Another preferred embodiment of the invention consists in using, in the compositions containing the pigment according to the invention, a tert-octylpropenamide acrylates copolymer such as the product sold under the name DERMACRYL 79 by the company NATIONAL STARCH. These compositions have an improved persistence of effect on exposure to water.

The compositions used for the temporary dyeing of keratinous fibers according to the invention can take various forms, such as the form of more or less thickened liquids, of creams, of gels or of sticks; the use of gels is, however, preferred.

The gels contain at least one suspending or thickening agent described above, in the aqueous, water/solvent(s) or solvent(s) media defined above.

The compositions intended for use for the temporary dyeing of keratinous fibers according to the invention can contain, in addition, various adjuvants customarily used in hair-care compositions. Among these adjuvants, there may be mentioned volatile or nonvolatile, insoluble or soluble silicones in the form of oils, gums, resins or powders, nonionic, anionic, cationic or amphoteric polymers; proteins, quaternized or otherwise; sunscreen agents; surfactants; antifoams; hydrating agents; hnnectants; emollients; vegetable or synthetic oils; preservatives, sequestering agents; antioxidants; pearlescence agents and perfumes; alkalinizing or acidifying agents; other pigments such as those described in the work COLOUR INDEX, except for zinc, cenium [sic], zirconium and titanium oxide nanopigments, as well as other direct dyes which are known generally in temporary dyeing.

The insoluble pigments resulting from the oxidative polymerization of the indole derivatives of formula (I) which are defined above are preferably used for dyeing hair. They are used especially for making white hairs less noticeable and more attractive. The application is followed by drying of the hair and styling.

These pigments may also be used in compositions intended for application to hairs such as eyelashes, in particular in mascara compositions.

The examples which follow are intended in the invention [sic], no limitation, however, being implied.

EXAMPLE 1

A hair gel of the following composition is prepared:

| | |
|---|---|
| Crosslinked polyacrylic acid sold under the name CARBOPOL 940 (MW 4,000,000) by the company GOODRICH | 0.3 g |
| Copolymer (65:35) of polyvinylpyrolidone and vinyl acetate, sold under the name PVP/VA S 630 by the company GAF | 4 g |
| Ethyl alcohol | 17 g |
| Pigment prepared according to Preparation Example 1 | 1 g |
| Triethanolamine qs | pH 7.5 |
| Water qs | 100 g |

The gel is used for the temporary dyeing of white hair. The hair is then dyed a natural gray.

The pigment obtained according to Preparation Example 1 may be replaced by the same quantity of pigment obtained according to Preparation Example 2, 3 or 4.

EXAMPLE 2

A hair gel of the following composition is prepared:

| | |
|---|---|
| - Emulsion of ammonium acrylate/crosslinked acrylamide copolymer, sold under the name PAS 5161 by the company HOECHST (containing 30% of copolymer AS) | 0.6 g AS |
| - Copolymer (65:35) of polyvinylpyrolidone and vinyl acetate, sold under the name PVP/VA S 630 by company GAF | 4 g |
| Pigment prepared according to Preparation Example 1 | 1 g |
| Triethanolamine qs | pH 7.5 |
| Water qs | 100 g |

The gel is applied to white hair, and imparts a temporary coloration which can be removed at the first shampooing.

EXAMPLE 3

A hair gel of the following composition is prepared:

| | |
|---|---|
| - Crosslinked copolymer of acrylic acid and ($C_{10}$–$C_{30}$) alkyl acrylate, sold under the name PEMULEN TR1 by the company GOODRICH (completely neutralized with triethanolamine) (before neutralization) | 0.5 g |
| - Aqueous acrylic latex sold at a concentration of 40% of AS under the name PRIMAL K3 by the company RHOM & HAAS | 1.3 g AS |
| - Copolymer (65:35) of polyvinylpyrolidone and vinyl acetate, sold under the name PVP/VA S 630 by the company GAF | 2 g |
| Pigment prepared according to Preparation Example 1 | 1 g |
| Triethanolamine qs | pH 7.5 |
| Preservative qs | |
| Water qs | 100 g |

The gel is applied to white hair, and imparts a temporary coloration which can be removed at the first shampooing.

EXAMPLE 4

A hair gel of the following composition is prepared:

| | |
|---|---|
| - Crosslinked copolymer of acrylic acid and ($C_{10}$–$C_{30}$) alkyl acrylate, sold under the name PEMULEN TR1 by the company GOODRICH, completely neutralized with triethanolamine (before neutralization) | 0.6 g |
| - Copolymer (65:35) of polyvinylpyrolidone and vinyl acetate, sold under the name PVP/VA S 630 by the company GAF | 2 g |
| Pigment prepared according to Prepartion Example 1 | 1 g |
| Triethanolamine qs | pH 7.5 |
| Preservative qs | |
| Water qs | 100 g |

The gel is applied to white hair, and imparts a temporary coloration which can be removed at the first shampooing.

EXAMPLE 5

A hair gel of the following composition is prepared:

| | |
|---|---|
| - Crosslinked copolymer of methacrylic acid and ethyl acrylate, sold in aqueous dispersion at a concentration of 38% of AS under the name VISCOATEX 538 by the company COATEX | 2.28 g AS |
| - Copolymer of hydroxyethylcellulose grafted by a free-radical method with diallyldimethylammonium chloride, sold by the company NATIONAL STARCH under the name CELQUAT L 200 | 1 g |
| Aminated silicone sold as a cationic emulsion at a concentration of 35% of AS under the name Emulsion DC 929 by the company DOW CORNING | 0.3 g AS |
| Pigment prepared according to Preparation Example 1 | 1 g |
| 2-Amino-2-methyl-1-propanol qs | pH 7.5 |
| Preservative, perfume qs | |
| Water qs | 100 g |

The gel is applied to white hair, and imparts a temporary coloration which can be removed at the first shampooing.

EXAMPLE 6

A mascara is prepared in the form of a gel having the following composition:

| | |
|---|---|
| - Micronized pigment originating from the polymerization of 5,6-dihydroyindole [sic] according to the process described in Example 1 | 10 g |
| - Carbopol 934 sold by the company GOODRICH | 0.80 g |
| Triethanoamine, 99% | 1.04 g AS |
| Polyvinlypyrrolidone | 0.45 g |
| Propylene glycol | 3.50 g |
| Vinyl alcohol/vinyl acetate copolymer | 2.09 g |
| D-Panthenol | 1 g |
| Preservative qs | |
| Water qs | 100 g |

EXAMPLE 7

| | |
|---|---|
| - Pigment originating from the polymerization of 5,6-dihydroxyindole, prepared according to Example 1 | 1 g |
| - Crosslinked copolymer of methacrylic acid and ethyl acrylate, sold in aqueous dispersion at a concentration of 38% of AS under the name VISCOATEX 538 by the company COATEX | 1.5 g AS |
| - Copolymer of hydroxyethylcellulose grafted by a free-radical method with diallyldimethylammonium chloride, sold by the company NATIONAL STARCH under the name CELQUAT L 200, made up in 5% aqueous solution | 1.5 g AS |
| Ethyl alcohol | 10 g |
| - Acrylates/t-octylpropenamide copolymer sold under the name DERMACRYL 79 by the company NATIONAL STARCH | 1.5 g |
| Stearyldimethylamine | 3.75 g |
| 2-Amino-2-methyl-1-propanol qs | pH 7.5 |
| Preservative, perfume, antifoam qs | |
| Water qs | 100 g |

Preparation Example 1

500 g (3.26 mol) of 5,6-dihydroxyindole are dissolved in 5 liters of water. 20 ml of 20% aqueous ammonia solution are added and the mixture is brought to 80° C. A mixture consisting of 750 ml of water and 750 g of 50% hydrogen peroxide solution is added dropwise at this temperature in the course of two hours. Heating is maintained for a further two hours after the addition is complete.

The black precipitate is drained and washed with water and then with alcohol. The product is dried under vacuum. 508 g of pigment are isolated.

This pigment perhaps [sic] micronized.

In a variant of this process, the precipitate is transferred in a wet medium to a ball mill before being washed with alcohol and dried. The pigment has an average particle size of less than 20 μm.

Preparation Example 2

90 g (0.6 mol) of 5,6-dihydroxyindole are dissolved at 20° C. in 6 liters of water.

With mechanical stirring, compressed air is injected for 168 hours.

The reaction medium is centrifuged.

The precipitate is washed with water and then drained.

350 g of wet black pigment with a dry matter content of 27.5% are obtained.

Preparation Example 3

50 g (0.32 mol) of 5,6-dihydroxyindole are dissolved in 500 ml of water, and the mixture is brought to 80° C.

A mixture consisting of 49 g of 50% hydrogen peroxide solution and 39 g of water is added in the course of 4 hours.

When the addition is complete, stirring is maintained for a further 2 hours.

The reaction medium is cooled to room temperature, and the precipitate formed is drained, washed with water and then dried under vacuum.

49.8 g of pigment are obtained.

Preparation Example 4

6 g (0.04 mol) of 5,6-dihydroxyindole are dissolved in 180 ml of water to which 20 ml of ethanol and 30 ml of 20-volumes hydrogen peroxide are added.

A solution of 2.5 g ($1.5 \times 10^{-2}$ mol) of potassium iodide dissolved in 25 ml of water is added to this mixture at room temperature in the course of 30 minutes.

Stirring is maintained for a further 3 hours when the addition is complete.

The precipitate is drained and washed with water and then with alcohol.

The product is dried under vacuum.

6 g of pigment are obtained.

We claim:

1. Process for the temporary dyeing of keratinous fibers, comprising applying to said fibers a composition containing, in a medium suitable for dyeing said fibers, an effective amount of particles consisting of an insoluble pigment to temporarily dye said fibers, said pigment consisting of the oxidative polymerization product of an indole compound corresponding to the formula (I)

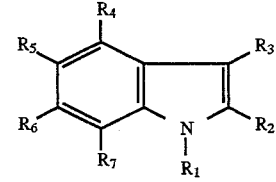

in which:

$R^1$ and $R^3$ represent, independently of one another, a hydrogen atom or a $C_1$–$C_4$ alkyl group;

$R^2$ represents a hydrogen atom, a $C_1$–$C_4$ alkyl group, a carboxyl group of a ($C_1$–$C_4$ alkoxy)carbonyl group;

$R^4$ and $R^7$ represent, independently of one another, a hydrogen atom, a hydroxyl group, a $C_1$–$C_4$ alkyl group, an amino group, a $C_1$–$C_4$ alkoxy group, a ($C_2$–$C_4$ acyl)oxy group or a ($C_2$–$C_4$ acyl)amino group;

$R^5$ represents a hydrogen atom, a hydroxyl group, a $C_1$–$C_4$ alkoxy group, a $C_1$–$C_4$ alkyl group, a halogen atom, an amino group, a ($C_2$–$C_{14}$ acyl)oxy group, a ($C_2$–$C_4$ acyl)amino group or a trimethylsilyloxy group;

$R^6$ represents a hydrogen atom, a hydroxyl group, a $C_1$–$C_4$ alkoxy group, an amino group, a ($C_2$–$C_4$ acyl)oxy group, a ($C_2$–$C_4$ acyl)amino group, a trimethylsilyloxy group or a hydroxy($C_2$–$C_4$ alkyl)amino group;

with the proviso that $R^5$ and $R^6$ cannot simultaneously designate a $C_1$–$C_4$ alkoxy radical;

it being possible for $R^5$ and $R^6$, together with the carbon atoms to which they are attached, to form a carbonyldioxy ring;

with the additional provisos that at least one of the radicals $R^4$ to $R^7$ represents a group OZ or $NHR^8$; at most one of the radicals $R^4$ to $R^7$ represents a group $NHR^8$; at most two of the radicals $R^4$ to $R^7$ represents a group OZ; when Z represents a hydrogen atom and there are two OZ groups, the two OZ groups are in positions 5 and 6; at least one of the radicals $R^4$ to $R^7$ represents a hydrogen atom; and, when only one of the radicals $R^4$ to $R^7$ represents a hydrogen atom, then only one radical from among $R^4$ to $R^7$ represents $NHR^8$ or OZ, the other radicals representing a $C_1$–$C_4$ alkyl group;

the radical $R^8$ of the group $NHR^8$ denoting a hydrogen atom or a $C_2$–$C_4$ acyl or $C_2$–$C_4$ hydroxyalkyl group, and the radical Z of the group OZ denoting a hydrogen atom, a $C_2$–$C_{14}$ acyl group, a $C_1$–$C_4$ alkyl group or a trimethylsilyl group, or their alkali metal, alkaline earth metal, ammonium or amine salts.

2. Process according to claim 1, wherein the indole compound of formula (I) is: 4-hydroxyindole, 5-hydroxyindole, 6-hydroxyindole, 7-hydroxyindole, 4-hydroxy-5-methoxyindole, 4-hydroxy-5-ethoxyindole, 2-carboxy-5-hydroxyindole, 5-hydroxy-6-methoxyindole, 6-hydroxy-7-methoxyindole, 5-methoxy-6-hydroxyindole, 5,6-dihydroxyindole, N-methyl-5,6-dihydroxyindole, 2-methyl-5,6-dihydroxyindole, 3-methyl-5,6-dihydroxyindole, 2,3-dimethyl-5,6-dihydroxyindole, 2-carboxy-5,6-hydroxyindole, 4-hydroxy-5-methylindole, 2-carboxy-6-hydroxyindole, 6-hydroxy-N-methylindole, 2-ethoxycarbonyl-5,6-dihydroxyindole, 4-hydroxy-7-methoxy-2,3-dimethylindole, 4-hydroxy-5-ethoxy-N-methylindole, 6-hydroxy-5-methoxy-2-methylindole, 6-hydroxy-5-methoxy-2,3-dimethylindole, 6-hydroxy-2-ethoxycarbonylindole, 7-hydroxy-3-methylindole, 5-hydroxy-6-methoxy-2,3-dimethylindole, 5-hydroxy-3-methylindole, 5-acetoxy-6-hydroxyindole, 5-hydroxy-2-ethoxycarbonylindole, 6-hydroxy-2-carboxy-5-methylindole, 6-hydroxy-2-ethoxycarbonyl-5-methoxyindole, 6-[N-(β-hydroxyethyl)amino]-indole, 4-aminoindole, 5-aminoindole, 6-aminoindole, 7-aminoindole, N-methyl-6-(β-hydroxyethylamino)indole, 6-amino-2,3-dimethylindole, 6-amino-2,3,4,5-tetramethylindole, 6-amino-2,3,4-trimethylindole, 6-amino-2,3,5-trimethylindole, 6-amino-2,3,6-trimethylindole, 5,6-diacetoxyindole, 5-methoxy-6-acetoxyindole, 5,6-trimethylsilyloxyindole, 5,6-dihydroxyindole phosphoric ester, 5,6-dibenzyloxyindole or the addition salts of these compounds.

3. Process according to claim 1, wherein the indole compound is: 5,6-dihydroxyindole, 6-hydroxyindole, 7-hydroxyindole, 2-methyl-5,6-dihydroxyindole hydrobromide, 7-aminoindole, 3-methyl-5,6-dihydroxyindole, 4-hydroxy-5-methoxyindole or 2,3-dimethyl-5-methoxy-6-hydroxyindole.

4. Process according to claim 1, wherein the oxidative polymerization to form the pigment is performed in an aqueous, water/solvent or solvent medium in the air, or in the presence or absence of an alkaline agent, an oxidizing agent or a mixture thereof.

5. Process according to claim 4, wherein the oxidizing agent is hydrogen peroxide, hydrogen peroxide in the presence of an alkaline agent, hydrogen peroxide used in the presence of an iodide ion, periodic acid, its water-soluble salts or its derivatives, permanganates, dichromates, sodium hypochloride, azunonium persulfate or sodium nitrite.

6. Process according to claim 4, wherein the oxidizing agent is ortho- or para-benzoquinones, ortho- or para-benzoquinone mono- or diimines, 1,2- or 1,4-naphthoquinone or 1,2- or 1,4-naphthoquinone mono- or diimines.

7. Process according to claim 1, wherein the oxidative polymerization is performed in a medium which comprises water, solvents, or mixtures thereof, hydrogen peroxide, and aqueous ammonia.

8. Process according to claim 1, wherein the pigment is in the form of particles and the particle size of the pigment particles is such that 90% of particles have a diameter of less than 100 µm.

9. Process according to claims 1, wherein the pigment resulting from the oxidative polymerization of the indole compounds of formula (I) has a particle size such that the average diameter of the particles is less than 50 µm.

10. Process according to claim 1, wherein the insoluble pigment resulting from the oxidative polymerization of indole derivatives of formula (I) is present in the composition in a proportion of between 0.05 and 10% by weight relative to the total weight of the composition.

11. Process according to claim 10, wherein the composition contains an aqueous medium which can contain one or more lower alcohols, polyols, glycol ethers, esters or mixtures thereof.

12. Process according to claim 1, wherein the composition contains a suspending or thickening agent enabling the insoluble pigments to be distributed homogeneously in the composition and on the treated fibers.

13. Process according to claim 12, wherein the suspending or thickening agent is cellulose derivatives, biopolysaccharides, guar gum or inorganic thickeners.

14. Process according to claim 1, wherein the composition contains a film-forming latex.

15. Composition for the temporary dyeing of keratinous fibers, comprising, in a medium suitable for temporary dyeing, an effective amount of particles consisting of an insoluble pigment to temporarily dye said fibers, said pigment consisting of the oxidative polymerization product of indole derivatives corresponding to the formula (I)

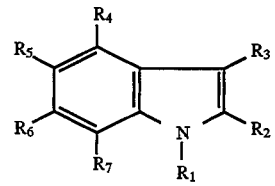

in which:

$R^1$ and $R^3$ represent, independently of one another, a hydrogen atom or a $C_1$–$C_4$ alkyl group;

$R^2$ represents a hydrogen atom, a $C_1$–$C_4$ alkyl group, a carboxyl group of a ($C_1$–$C_4$ alkoxy)carbonyl group;

$R^4$ and $R^7$ represent, independently of one another, a hydrogen atom, a hydroxyl group, a $C_1$–$C_4$ alkyl group, an amino group, a $C_1$–$C_4$ alkoxy group, a ($C_2$–$C_4$ acyl)oxy group or a ($C_2$–$C_4$ acyl)amino group;

$R^5$ represents a hydrogen atom, a hydroxyl group, a $C_1$–$C_4$ alkoxy group, a $C_1$–$C_4$ alkyl group, a halogen atom, an amino group, a ($C_2$–$C_{14}$ acyl)oxy group, a ($C_2$–$C_4$ acyl)amino group or a trimethylsilyloxy group;

$R^6$ represents a hydrogen atom, a hydroxyl group, a $C_1$–$C_4$ alkoxy group, an amino group, a ($C_2$–$C_4$ acyl)oxy group, a ($C_2$–$C_4$ acyl)amino group, a trimethylsilyloxy group or a hydroxy($C_2$–$C_4$ alkyl)amino group;

with the proviso that $R^5$ and $R^6$ cannot simultaneously designate a $C_1$–$C_4$ alkoxy radical;

it being possible for $R^5$ and $R^6$, together with the carbon atoms to which they are attached, to form a carbonyldioxy ring; with the additional provisos that at least one of the radicals $R^4$ to $R^7$ represents a hydrogen atom; when only one of the radicals $R^4$ to $R^7$ represents a hydrogen atom, then only one radical from among $R^4$ to $R^7$ represents $NHR^8$ or OZ, the other radicals representing a $C_1-C_4$ alkyl group;

the radical $R^8$ of the group $NHR^8$ denoting a hydrogen atom or a $C_2-C_4$ acyl or $C_2-C_4$ hydroxyalkyl group, and the radical Z of the group OZ denoting a hydrogen atom, a $C_2-C_{14}$ acyl group, a $C_1-C_4$ alkyl group or a trimethylsilyl group, or their alkali metal, alkaline earth metal, ammonium or amine salts, and at least one suspending or thickening agent selected from carboxymethylcellulose, hydroxyethylcellulose, or hydroxypropylcellulose; xanthan gums, sceroglucans, or guar gum; inorganic thickeners; crosslinked or uncrosslinked products resulting from the ionic interaction of a cationic polymer, formed from a copolymer of cellulose or of a cellulose derivative grafted with a water-soluble quaternary ammonium monomer salt, and a carboxylic anionic polymer; aqueous dispersions of ammonium acrylate/acryl-amide copolymers crosslinked with a crosslinking agent containing olefinic polymerization, dispersed in a water-in-oil emulsion; crosslinked or uncrosslinked copolymers of methyl vinyl ether and maleic anhydride; crosslinked polyacrylic acids; or crosslinked copolymers of acrylic acid and long-chain ($C_{10}-C_{30}$) alkyl methacrylate or acrylate.

16. Composition according to claim 15, wherein the suspending or thickening agent is present in proportions of between 0.05 and 10% by weight relative to the total weight of the composition.

17. Composition for the temporary dyeing of keratinous fibers, comprising, in a medium suitable for temporary dyeing, an effective amount of particles consisting of an insoluble pigment to temporarily dye said fibers, said pigment consisting of the oxidative polymerization product of an indole compound corresponding to the formula (I)

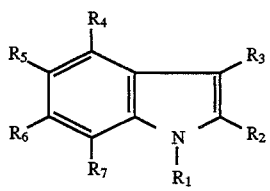

in which:

$R^1$ and $R^3$ represent, independently of one another, a hydrogen atom or a $C_1-C_4$ alkyl group;

$R^2$ represents a hydrogen atom, a $C_1-C_4$ alkyl group, a carboxyl group of a ($C_1-C_4$ alkoxy)carbonyl group;

$R^4$ and $R^7$ represent, independently of one another, a hydrogen atom, a hydroxyl group, a $C_1-C_4$ alkyl group, an amino group, a $C_1-C_4$ alkoxy group, a ($C_2-C_4$ acyl)oxy group or a ($C_2-C_4$ acyl)amino group;

$R^5$ represents a hydrogen atom, a hydroxyl group, a $C_1-C_4$ alkoxy group, a $C_1-C_4$ alkyl group, a halogen atom, an amino group, a ($C_2-C_{14}$ acyl)oxy group, a ($C_2-C_4$ acyl)amino group or a trimethylsilyloxy group;

$R^6$ represents a hydrogen atom, a hydroxyl group, a $C_1-C_4$ alkoxy group, an amino group, a ($C_2-C_4$ acyl)oxy group, a ($C_2-C_4$ acyl)amino group, a trimethylsilyloxy group or a hydroxy ($C_2-C_4$ alkyl) amino group;

with the proviso that $R^5$ and $R^6$ cannot simultaneously designate a $C_1-C_4$ alkoxy radical;

it being possible for $R^5$ and $R^6$, together with the carbon atoms to which they are attached, to form a carbonyl-dioxy ring;

with the additional provisos that at least one of the radicals $R^4$ to $R^7$ represents a group OZ or $NHR^8$; at most one of the radicals $R^4$ to $R^7$ represents $NHR^8$; at most two of the radicals $R^4$ to $R^7$ represents OZ; when Z represents a hydrogen atom and there are two OZ groups, the two OZ groups are in positions 5 and 6; at least one of the radicals $R^4$ to $R^7$ represents a hydrogen atom; and, in the case where only one of the radicals $R^4$ to $R^7$ represents a hydrogen atom, then only one radical from among $R^4$ to $R^7$ represents $NHR^8$ or OZ, the other radicals representing a $C_1-C_4$ alkyl group;

the radical $R^8$ of the group $NHR^8$ denoting a hydrogen atom or a $C_2-C_4$ acyl or $C_2-C_4$ hydroxyalkyl group, and the radical Z of the group OZ denoting a hydrogen atom, a $C_2-C_{14}$ acyl group, a $C_1-C_4$ alkyl group or a trimethylsilyl group, or their alkali metal, alkaline earth metal, ammonium or amine salts, and a film-forming latex.

18. Composition according to claim 17, wherein the film-forming latex is homopolymers or copolymers of vinyl acetate; homopolymers or copolymers derived from acrylic acid; polyurethanes; butadiene/styrene copolymers, carboxylated or not carboxylated; butadiene/acrylonitrile copolymers, carboxylated or not carboxylated; styrene/acrylic esters copolymers; vinyl acetate/acrylic esters copolymers; styrene/butadiene/vinylpyridine terpolymers; or copolymers of vinyl chloride or of vinylidene chloride.

19. Composition according to claim 15, wherein the temporary dyeing composition further contains volatile or nonvolatile, insoluble or soluble silicones in the form of oils, gums, resins or powders; nonionic, anionic, cationic or amphoteric polymers; proteins, quaternized or not quaternized; sunscreen agents; surfactants; antifoams; hydrating agents; humectants; emollients; vegetable or synthetic oils; preservatives; sequestering agents; antioxidants; pearlescence agents; perfumes; alkalinizing or acidifying agents; pigments; or direct dyes.

20. Process according to claim 8, wherein the particle size of the pigment particles is such that 90% of particles have a diameter of less than 50 μm.

21. Process according to claim 9, wherein the particle size is such that the average diameter of the particles is less than 20 μm.

22. Process according to claim 10, wherein the insoluble pigment is used in the composition in a proportion of between 0.2 and 2% by weight relative to the total weight of the composition.

* * * * *